(12) United States Patent
Chebator (10) Patent No.: US 8,152,778 B2
(45) Date of Patent: Apr. 10, 2012

(54) DEVICE FOR INTERFACING WITH STANDARD LUER LOCK SYRINGES

(75) Inventor: Casey Chebator, Weymouth, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 212 days.

(21) Appl. No.: 12/565,044

(22) Filed: Sep. 23, 2009

(65) Prior Publication Data

US 2010/0082015 A1     Apr. 1, 2010

Related U.S. Application Data (60) Provisional application No. 61/101,400, filed on Sep. 30, 2008.

(51) Int. Cl.
*A61M 5/315* (2006.01)
(52) U.S. Cl. ......... 604/231; 604/191; 604/218; 604/236
(58) Field of Classification Search .................. 604/187, 604/191, 218, 231, 232, 234, 236, 240, 241, 604/533, 534, 535
See application file for complete search history.

(56) References Cited

U.S. PATENT DOCUMENTS

| | | |
|---|---|---|
| 3,749,084 A | 7/1973 | Cucchiara |
| 4,439,184 A | 3/1984 | Wheeler |
| 4,702,737 A | 10/1987 | Pizzino |
| 4,715,854 A | 12/1987 | Vaillancourt |
| 4,929,230 A | 5/1990 | Pfleger |
| 5,298,024 A | 3/1994 | Richmond |
| 5,354,284 A | 10/1994 | Haber et al. |
| 5,501,673 A | 3/1996 | Hjertman et al. |
| 5,599,312 A | 2/1997 | Higashikawa |
| 5,697,915 A | 12/1997 | Lynn |
| 5,704,918 A | 1/1998 | Higashikawa |
| 5,716,338 A | 2/1998 | Hjertman et al. |
| 5,720,731 A | 2/1998 | Aramata et al. |
| 5,743,879 A | 4/1998 | Kriesel |
| 5,788,670 A | 8/1998 | Reinhard et al. |
| 5,830,193 A | 11/1998 | Higashikawa |
| 5,911,703 A | 6/1999 | Slate et al. |
| 5,968,018 A | 10/1999 | Freeman et al. |
| 5,971,953 A | 10/1999 | Bachynsky |
| 6,270,482 B1 | 8/2001 | Rosoff et al. |

(Continued)

FOREIGN PATENT DOCUMENTS

EP    0 072 058    2/1983

(Continued)

OTHER PUBLICATIONS

European Search Report dated Jan. 4, 2010 for EP 09171240.6-2320, 8 pages.

*Primary Examiner* — Bhisma Mehta
(74) *Attorney, Agent, or Firm* — Lisa E. Winsor, Esq.

(57) ABSTRACT

An interface device is described which includes a body defining one or more cylindrical bores which are dimensioned to receive a standard luer lock syringe. Each bore includes a plunger movably positioned therein from a retracted position to an advanced position. The plunger and the distal end of the bore defines a first fluid reservoir and the standard syringe assembly defines a second fluid reservoir. The interface device and the syringe assembly are operable to sequentially deliver multiple fluids from the interface device to a catheter assembly.

13 Claims, 6 Drawing Sheets

U.S. PATENT DOCUMENTS

| | | |
|---|---|---|
| 6,328,229 B1 | 12/2001 | Duronio et al. |
| 6,723,074 B1 | 4/2004 | Halseth |
| 6,740,062 B2 | 5/2004 | Hjertman |
| 6,866,653 B2 | 3/2005 | Bae |
| 6,945,962 B2 | 9/2005 | Koenig et al. |
| 6,997,910 B2 | 2/2006 | Howlett et al. |
| 7,001,362 B2 | 2/2006 | Vincent |
| 7,033,337 B2 | 4/2006 | Hjertman |
| 7,077,827 B2 | 7/2006 | Greenfield |
| 7,104,971 B2 | 9/2006 | Hjertman |
| 2002/0029019 A1 | 3/2002 | Rosoff et al. |
| 2002/0035351 A1 | 3/2002 | Lodice |
| 2002/0052579 A1 | 5/2002 | Sogaro |
| 2002/0087122 A1 | 7/2002 | Sogaro |
| 2002/0099384 A1 | 7/2002 | Scribner et al. |
| 2002/0138043 A1 | 9/2002 | Tanaka et al. |
| 2003/0004467 A1 | 1/2003 | Musick et al. |
| 2003/0105433 A1 | 6/2003 | Ruben |
| 2003/0167041 A1 | 9/2003 | Rosoff et al. |
| 2003/0199816 A1 | 10/2003 | Ramming |
| 2003/0236503 A1 | 12/2003 | Koenig et al. |
| 2004/0044316 A1 | 3/2004 | Greenfield |
| 2004/0097875 A1 | 5/2004 | Bae |
| 2004/0116871 A1 | 6/2004 | Vincent |
| 2005/0240157 A1 | 10/2005 | Amisar et al. |
| 2005/0245880 A1 | 11/2005 | Howlett et al. |
| 2007/0161961 A1* | 7/2007 | Hasegawa ............... 604/187 |
| 2007/0208295 A1 | 9/2007 | Oloodmiyazdi |
| 2008/0114304 A1 | 5/2008 | Nalesso et al. |

FOREIGN PATENT DOCUMENTS

| | | |
|---|---|---|
| EP | 0 219 899 | 4/1987 |
| FR | 2 581 547 | 11/1986 |
| WO | WO 2008/137578 | 11/2008 |

* cited by examiner

DEVICE FOR INTERFACING WITH STANDARD LUER LOCK SYRINGES

This application claims priority from U.S. Provisional Application Ser. No. 61/101,400 which was filed on Sep. 30, 2008, and is incorporated. herein by reference in its entirety.

BACKGROUND

1. Technical Field

The present disclosure is directed generally to an interface device for use with standard luer lock syringes. More particularly, the present disclosure is directed to an interface device capable of interfacing with standard luer lock syringes to sequentially deliver multiple fluids from the device to a medical access device.

2. Background Of Related Art

Numerous techniques are employed for the administration of "medical liquids" (e.g. liquid medication and flush/lock solutions) to a patient. In particular, where repeated medication infusions are required, medical liquids are often administered via the use of a central venous access catheter (CVAD) that is fluidly interconnected or interconnectable to one or more medical liquid sources via an associated tubing line set. Typically, the CVAD is inserted into the vein of a patient and left there for multiple intravenous (IV) infusions during an extended course of medication therapy.

It is usual practice to purge the CVAD with a flush solution (e.g. a saline solution) prior to and at the completion of a given liquid medication infusion. Pre-infusion flushing verifies that the vascular catheter is primed and clear of obstructions. Post infusion flushing/locking not only flushes through any remaining liquid medication to achieve the desired therapeutic effect, but also reduces the risk of CVAD blockage.

Typically, post infusion flushing/locking procedures involve a two step procedure wherein in a first step, a flush solution, e.g., saline, is infused into a CVAD to flush any medication remaining in the CVAD from the CVAD into a patient, and in a second step, a lock solution, e.g., heparin, is infused into the CVAD to prevent clotting of the CVAD. The lock solution may also include anti-microbial agents to reduce the risk of infection to the patient from bacterial colonization of the CVAD.

A number of approaches are currently utilized to perform flushing/locking procedures including the use of multiple prefilled syringes, which subjects the CVAD to multiple connections thus, increasing the risk of patient exposure to contaminants.

It would be desirable to provide a device which could interface with a standard luer-lock syringe to facilitate performance of flushing/locking procedures using only a single connection to the CVAD.

SUMMARY

An interface device is disclosed which includes a body defining at least one substantially cylindrical bore having a first open end dimensioned to receive a standard syringe assembly and a second end defining an outlet channel. The body includes a side channel which extends through an inner sidewall of each of the at least one substantially cylindrical bores and communicates with the outlet channel. Each of the at least one substantially cylindrical bores includes a plunger movably positioned within the bore from a retracted position to an advanced position. Each plunger has a top surface adapted to engage a distal end of a standard syringe assembly, a bottom surface and a sidewall. The bottom surface of the plunger and a distal end of the respective at least one substantially cylindrical bore defines a first fluid reservoir. A plunger channel extends from the top surface of the plunger to the sidewall of the plunger. In the retracted position, the plunger channel is sealed by an inner sidewall of the body defining the at least one substantially cylindrical bore. In the advanced position, the plunger channel communicates with the respective side channel of the body.

In one embodiment, the top surface of each plunger includes a substantially annular lip which is positioned about an inlet end of the plunger channel and is dimensioned to engage a distal end of a standard syringe assembly. Each plunger may also have an annular channel defined about the sidewall of the plunger.

In one embodiment, an annular groove is formed in the sidewall defining the at least one substantially cylindrical bore. An inlet end of the side channel may be positioned within the annular groove.

In one embodiment, the body includes a connector positioned about the outlet channel. A flange may also be positioned about the first open end of the body.

In one embodiment, the at least one substantially cylindrical bore includes a plurality of substantially cylindrical bores.

A first fluid is provided within the fluid reservoir. The first fluid may be a flush solution, such as saline.

A method of infusing a catheter assembly is also disclosed which includes the steps of:

i) providing the interface device as recited in claim 1 having a first solution in the first reservoir; ii) positioning a first syringe assembly into a first of the at least one substantially cylindrical bore of the interface device, the syringe assembly defining a second fluid reservoir having a second solution therein; iii) securing the body of the interface device to a catheter assembly; iv) advancing the syringe assembly within the first cylindrical bore to move the plunger from its retracted position to its advanced position to dispense the first fluid from the first reservoir into the catheter assembly; and v) actuating a plunger assembly of the syringe assembly to dispense the second fluid from the second reservoir of the syringe assembly into the catheter assembly.

In one embodiment, the first fluid is a flush solution and the second fluid is a lock solution. The flush solution may be saline and the lock solution may be heparin.

In one embodiment, the method also includes the following steps: vi) positioning a second syringe assembly into a second of the at least one substantially cylindrical bores, the second substantially cylindrical bore having a second plunger and defining a third reservoir having a third fluid therein and the second syringe assembly defining a fourth reservoir having a fourth fluid therein; vii) advancing the second syringe assembly within the second substantially cylindrical bore to move the second plunger from its retracted position to its advanced position to dispense the third fluid from the third reservoir into the catheter assembly; and viii) actuating a second plunger assembly of the second syringe assembly to dispense the fourth fluid from the fourth fluid reservoir of the second syringe assembly into the catheter assembly.

BRIEF DESCRIPTION OF THE DRAWINGS

Various embodiments of the presently disclosed device for interfacing with standard luer lock syringes ("interface device") are disclosed herein with reference to the drawings, wherein.

DETAILED DESCRIPTION OF EMBODIMENTS

Embodiments of the presently disclosed interface device will now be described in detail with reference to the drawings wherein like reference numerals designate identical or corresponding elements in each of the several views. In this description, the term proximal is generally used to indicate the relative nearness of a referenced item to a user of the device and the term distal is used to indicate the relative remoteness of a referenced item to a user of the device.

Figure 1:
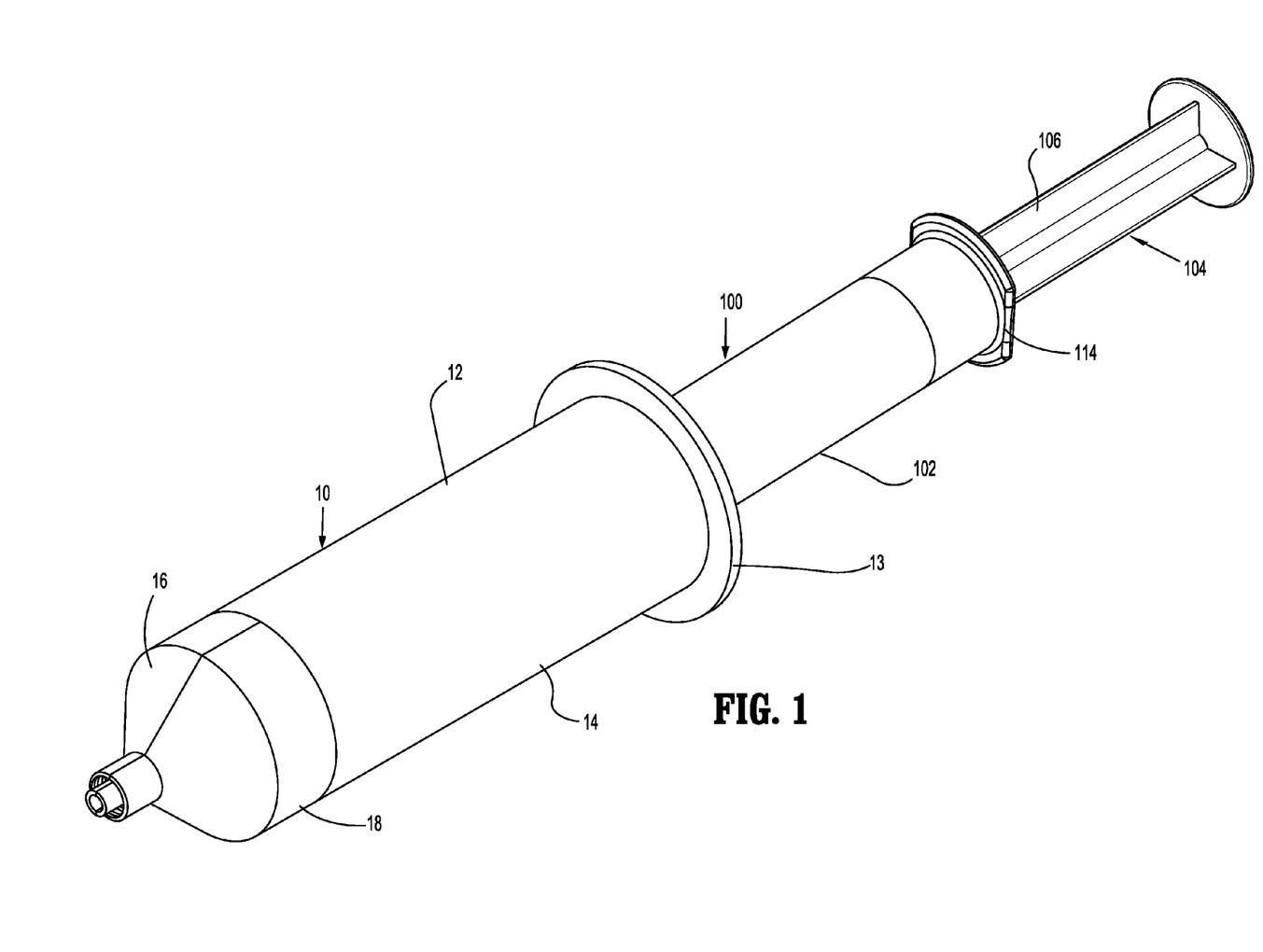
FIG. 1 is a side perspective view from the distal end of one embodiment of the presently disclosed interface device with a standard syringe assembly received therein.
Figure 2:
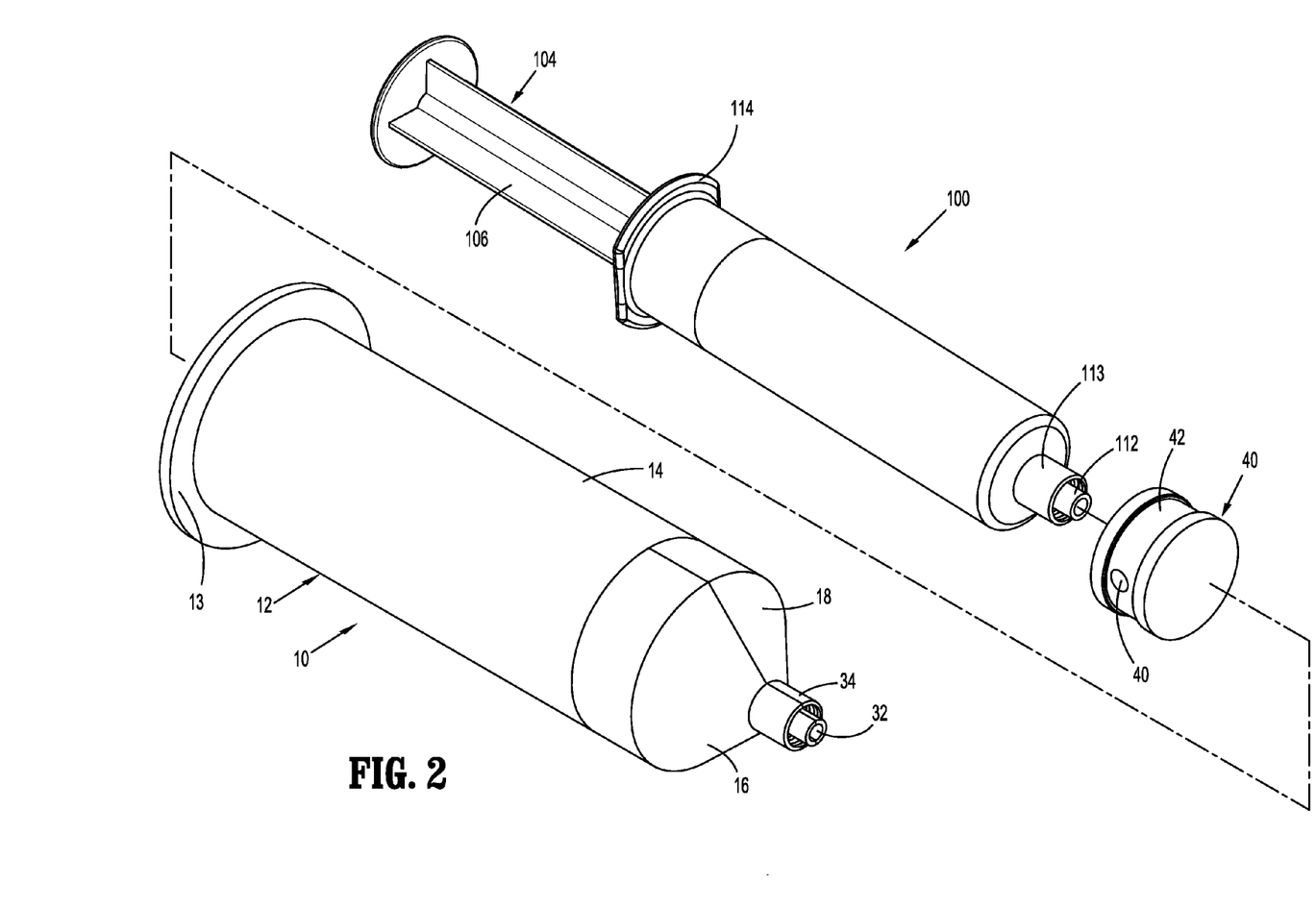
FIG. 2 is a side perspective exploded view of the interface device and syringe assembly shown in FIG. 1.
Figure 2A:
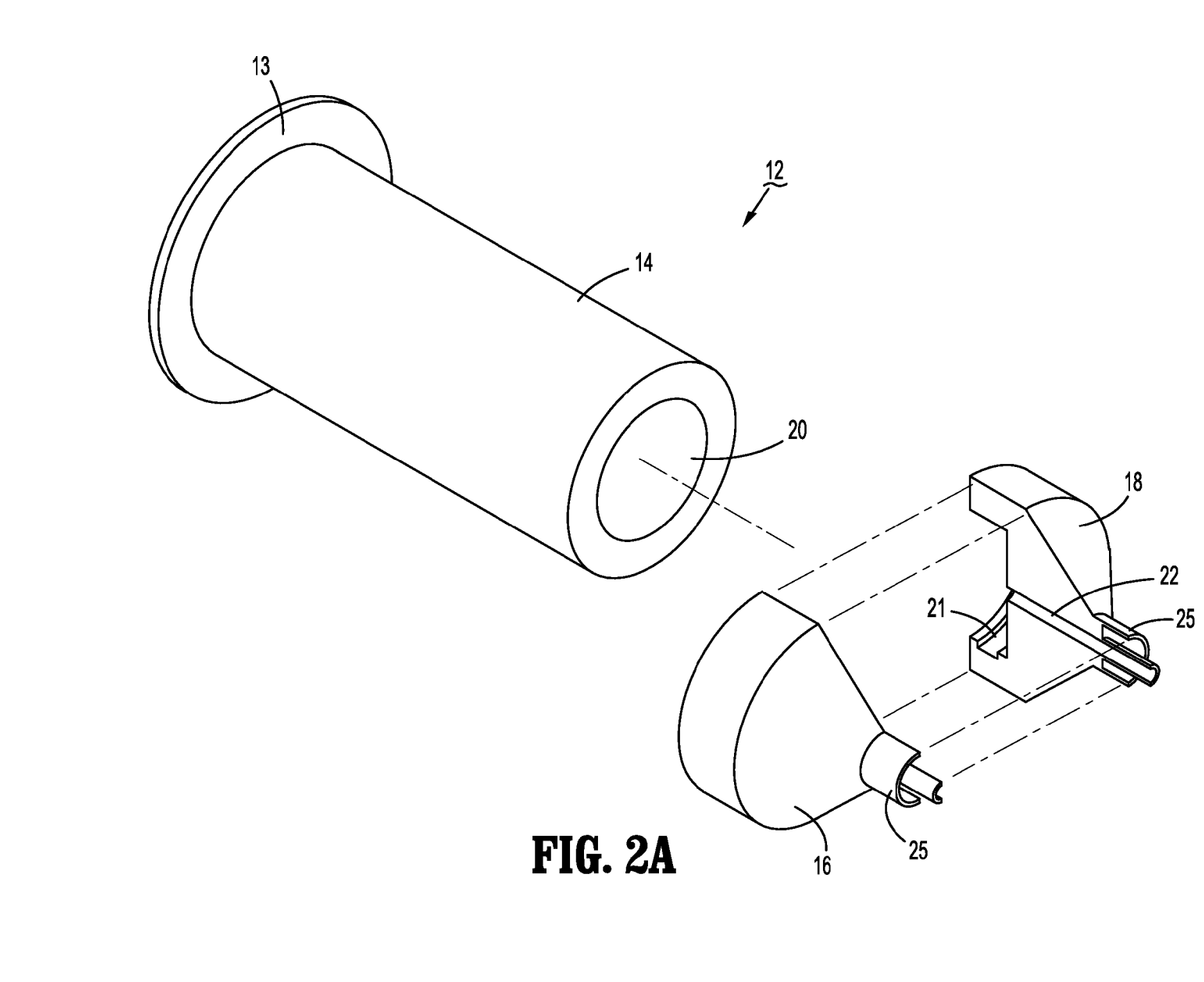
FIG. 2A is a side, perspective exploded view of the body of the interface device shown in FIG. 2.
Figure 3:
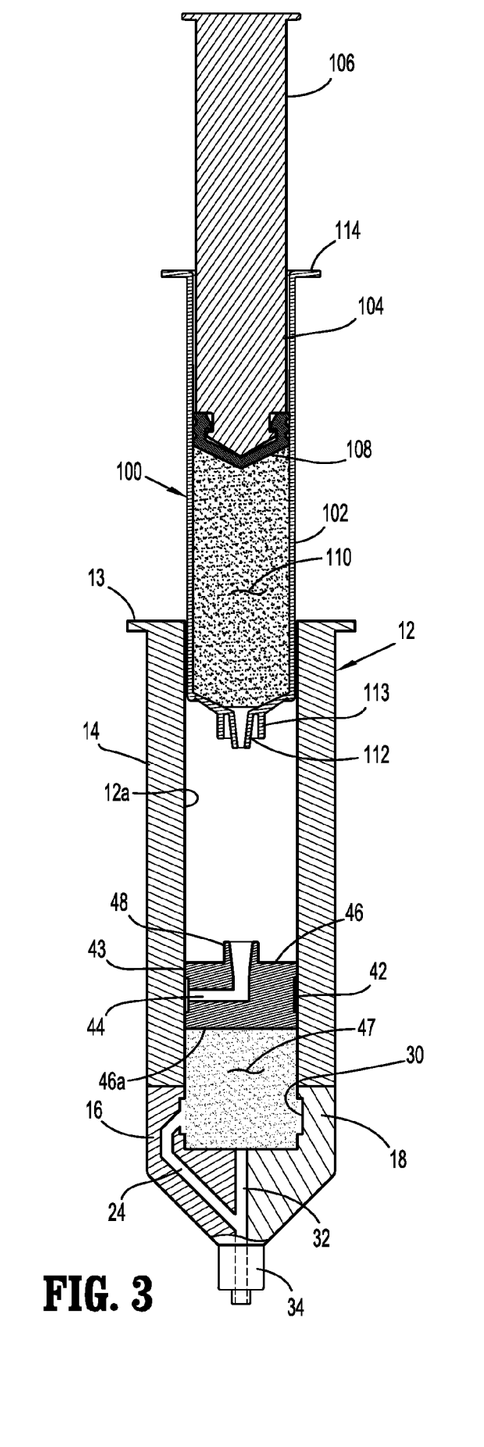
FIG. 3 is a side cross-sectional view of the interface device with a syringe assembly partially received therein.

FIGS. 1-3 illustrate one embodiment of the presently disclosed interface device, shown generally as 10, in conjunction with a standard syringe assembly 100. Syringe assembly 100 is known in the medical art and will only be described in detail necessary to facilitate description of interface device 10.

Referring to FIGS. 1-2A, interface device 10 includes a body 12 including a proximal body portion 14, a distal body half-section 16 and a distal body half-section 18. Proximal portion 14 includes a proximal gripping flange 13 and defines a cylindrical bore 20 (FIG. 2A). Each distal half-section 16 and 18 defines a semi-annular groove 21 and a longitudinal groove 22. Distal half-section 16 further defines a side channel 24 (FIGS. 3 and 4) which extends from within semi-annular groove 21 and intersects longitudinal groove 22 at a location proximal to a distal end of longitudinal groove 22. The distal end of each distal half-section 16 and 18 further defines connector half-sections 25.

Figure 4:
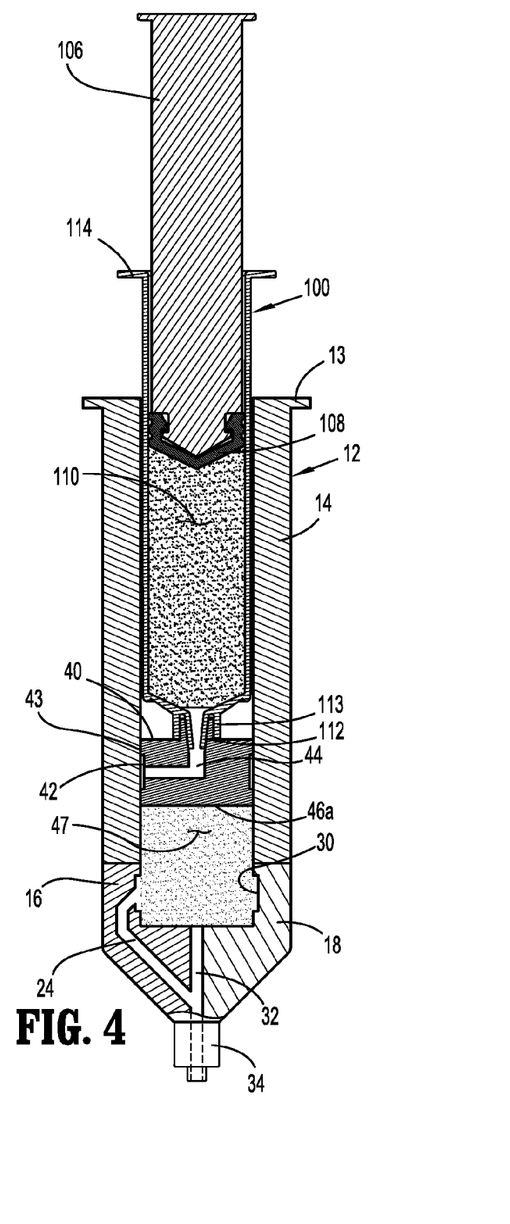
FIG. 4 is a side cross-sectional view of the interface device with a syringe assembly received therein prior to injection.

Referring to FIGS. 3 and 4, distal half-sections 16 and 18 are secured to a distal end of proximal portion 14 of body 12 and to each other using a known fastening technique, e.g., sonic welding, adhesives, etc., such that semi-annular grooves 21 define an annular groove 30, longitudinal grooves 22 define an outlet channel 32 and connector half-sections 25 define a male luer-type connector 34 or similar structure.

Referring to FIGS. 2-3, a plunger 40 is slidably positioned within cylindrical bore 20 of body 12. Plunger 40 is substantially cylindrical and is dimensioned to slidably and sealingly engage an inner wall 12a of body 12. Plunger 40 defines an annular channel 42 about its sidewall 43 and a channel 44 which extends from a top surface 46 of plunger 40 to annular channel 42. A bottom surface 46a of plunger 40 defines a first fluid reservoir 47 with the distal end of body 12. Top surface 46 of plunger 40 includes a luer-type connector 48 positioned about an inlet end of channel 44. Connector 48 is dimensioned to be engaged by a corresponding luer-type connector on the distal end of a standard syringe assembly 100 in a fluid tight manner as will be discussed in further detail below. Referring to FIG. 3, syringe assembly 100 includes a syringe body 102 and a plunger assembly 104. Syringe body 102 is dimensioned to be tightly received within cylindrical bore 20 of body 12 of interface device 10. Plunger assembly 104 includes a plunger rod 106 and a plunger head 108 which is secured to a distal end of plunger rod 106 and is slidably positioned within syringe body 102. Syringe body 102 and a distal face of plunger head 108 define a fluid reservoir 110. A distal end of syringe body 102 defines a fluid outlet 112 and a luer-type connector 113.

Referring to FIGS. 3-6, in use a standard syringe assembly 100 is positioned within cylindrical bore 20 of interface device 10 such that fluid outlet 112 is received within channel 44 of plunger 40 and connector 48 of plunger 40 engages connector 113 of syringe 100. (FIG. 4). Although not shown, a cap can be secured to connector 34 on the distal end of interface device 10 to seal outlet channel 32 until immediately prior to use of interface device 10.

Figure 5:
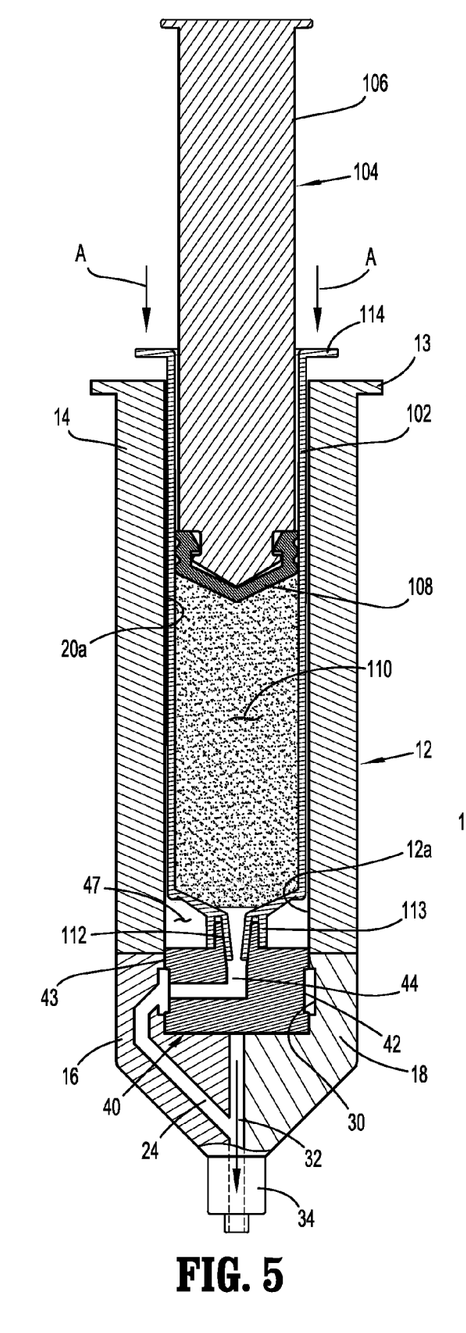
FIG. 5 is a side cross-sectional view of the interface device and syringe assembly after a first stage of injection.

Referring to FIG. 5, after syringe assembly 100 has been positioned within cylindrical bore 20 of body 12, the cap (not shown) positioned over outlet channel 32 can be removed and connector 34 of interface device 10 can be secured to a central venous access device (not shown) or the like. Next, syringe body 102 which includes a gripping flange 114 can be pressed into cylindrical bore 20 of body 12 in the direction indicated by arrows "A" in FIG. 5. When syringe body 102 moves into cylindrical bore 20 of body 12, plunger 40 is forced from a retracted position (FIG. 4) to an advanced position (FIG. 5) to dispense a first fluid from reservoir 47 of interface device 10 via fluid outlet channel 32. As plunger 40 moves from the retracted position towards the advanced position, annular channel 42 and channel 44 which communicate with reservoir 110 within syringe body 102 are sealed by the inner wall 20a defining cylindrical bore 20. Thus, a second fluid within reservoir 110 of syringe body 102 is prevented from being dispensed from reservoir 110.

Referring again to FIG. 5, when plunger 40 nears the advanced position, annular channel 42 communicates with annular groove 30 of body 12. When channel 42 communicates with annular groove 30, reservoir 110 of syringe assembly 100 is in communication with outlet channel 32 via channel 44, annular channel 42, annular groove 30 and channel 24. It is also envisioned that the use of either annular channel 42 or annular groove 30 in the absence of the other would be capable of establishing communication between channel 44 and channel 24.

Figure 6:
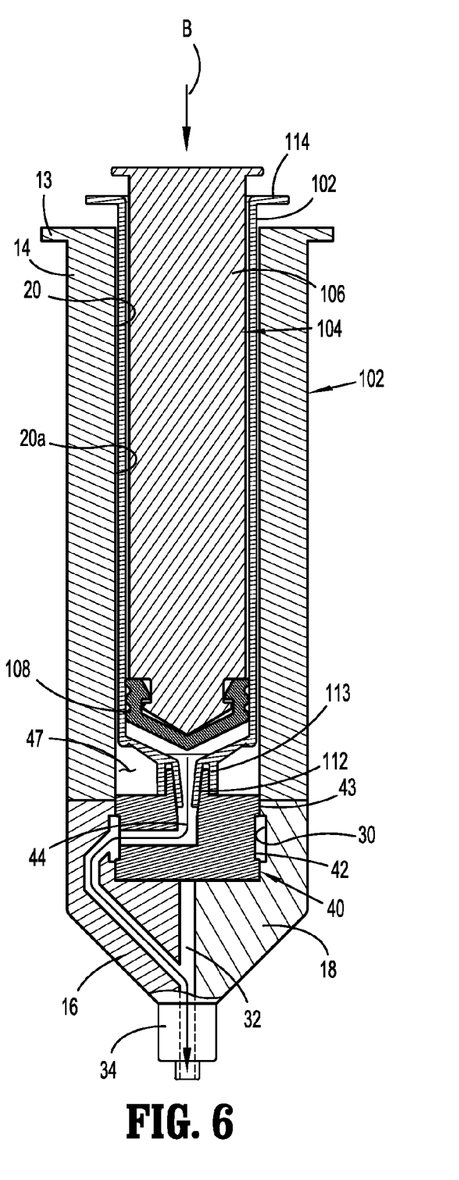
FIG. 6 is a side cross-sectional view of the interface device and syringe assembly after a second stage of injection.

Referring to FIG. 6, when plunger 40 is in the advanced position and plunger assembly 104 is moved from its retracted position (FIG. 5) to its advanced position in the direction indicated by arrow "B" in FIG. 6, the second fluid located within reservoir 110 of syringe body 102 is forced from reservoir 110 through fluid outlet 112 of syringe body 102. Fluid flowing from outlet 112 flows through channel 44 of plunger 40 and channel 24 of body 12 of interface device 10, and through fluid outlet 32 of device 10.

In one embodiment, the first fluid within reservoir 47 of device 10 is a flush solution such as saline and the second fluid within reservoir 110 of syringe body 102 is a lock solution such as heparin. As discussed above, a flush solution is used to flush medication remaining in a catheter from the catheter into a patient whereas a lock solution, such as heparin, is used to maintain the patency of a catheter lumen while minimizing the risk of infection to a patient. Although the use of interface device 10 has been described for use with a flush solution and a standard syringe assembly having a lock solution, it is envisioned that other fluids can be dispensed sequentially with the presently disclosed interface device and standard syringe assembly. It is also envisioned that reservoir 47 may be prefilled with the first fluid during manufacture of device 10.

Figure 7:
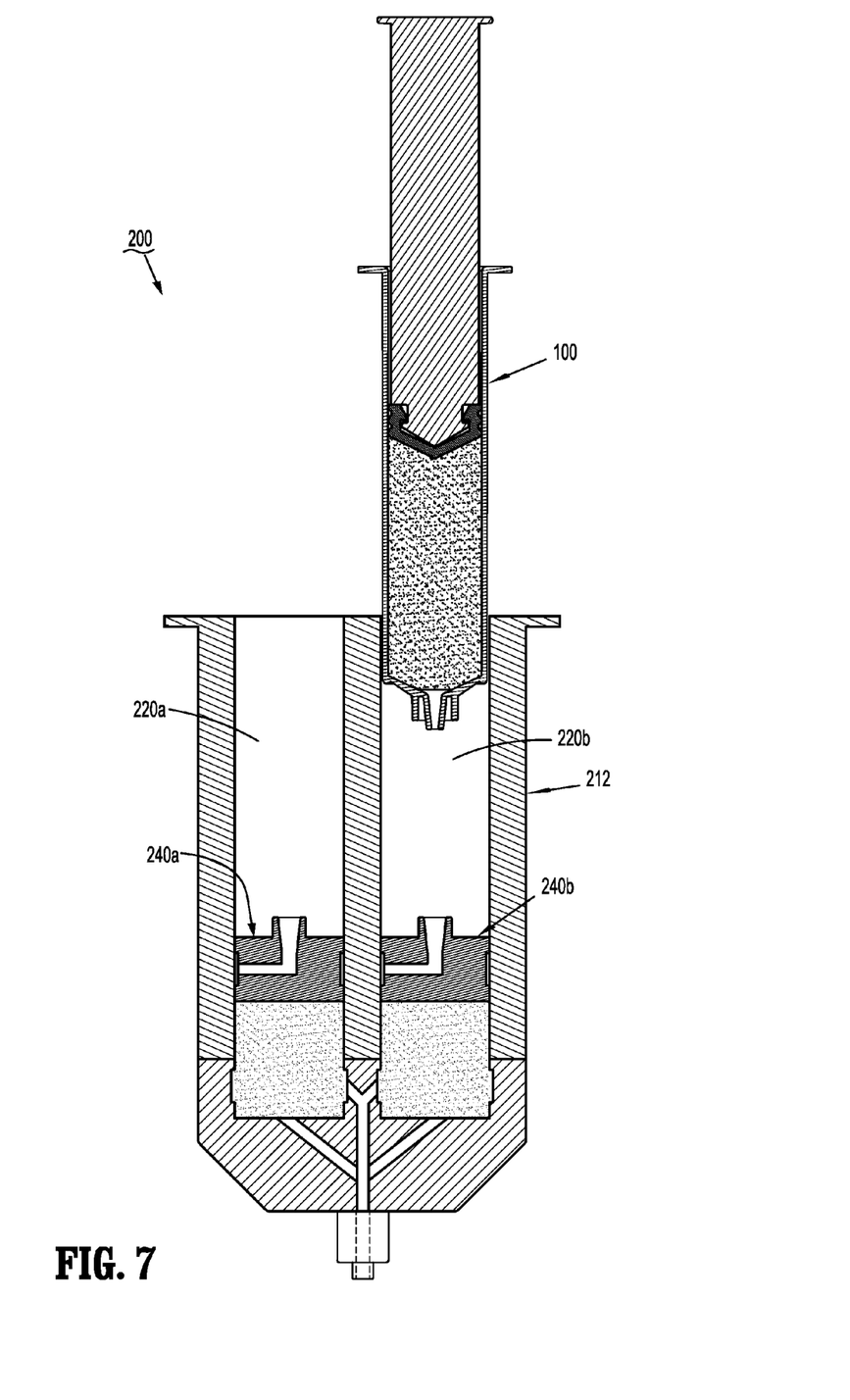
FIG. 7 is a side cross-sectional view of another embodiment of the presently disclosed interface device with a syringe assembly partially received therein.

FIG. 7 illustrates an alternative embodiment of the presently disclosed interface device shown generally as 200. Interface device 200 is substantially similar to interface device 10 but includes a body 212 defining two cylindrical bores 220a and 220b and a plunger 240a and 240b positioned within each cylindrical bore 220a and 220b, respectively. Each cylindrical bore 220a and 220b is dimensioned to receive a syringe assembly 100 as described above. Plungers 240a and 240b are identical to plunger 40 (FIG. 5) described above and will not be described in further detail herein. Interface device 200 in association with two syringe assemblies 100 functions to inject four fluids sequentially into a catheter (not shown) in the manner described above with respect to interface device 10.

It will be understood that various modifications may be made to the embodiments disclosed herein. For example, the interface device may include three or more cylindrical bores and plungers and/or consist of single piece construction. Therefore the above description should not be construed as limiting, but merely as exemplifications of embodiments. Those skilled in the art will envision other modifications within the scope and spirit of the claims appended hereto.

What is claimed is:

1. An interface device comprising:
a body defining a substantially cylindrical bore having a first open end dimensioned to receive a standard syringe assembly having a syringe body and a plunger assembly, and a second end defining an outlet channel, the body including a side channel extending through a sidewall of the substantially cylindrical bore, the side channel being in fluid communication with the outlet channel and the substantially cylindrical bore;
the substantially cylindrical bore including a plunger movably positioned within the bore from a retracted position to an advanced position, each plunger having a top surface adapted to engage a distal end of a standard syringe assembly, a bottom surface and a sidewall, the bottom surface of the plunger and a distal end of the substantially cylindrical bore defining a first reservoir, a plunger channel extending through the plunger from the top surface of the plunger to the sidewall of the plunger, wherein in the retracted position, the plunger channel is sealed by the sidewall of the bore, and in the advanced position, the plunger channel communicates with the side channel of the body.

2. The interface device according to claim 1, wherein the top surface of each plunger includes a connector which is positioned about an inlet end of the plunger channel, the connector being dimensioned to engage a distal end of a standard syringe assembly.

3. The interface device according to claim 1, wherein each plunger has an annular channel defined about the sidewall of the plunger.

4. The interface device according to claim 1, wherein an annular groove is formed in the sidewall of the bore, an inlet end of the side channel being positioned within the annular groove.

5. The interface device according to claim 1, wherein the body includes a connector positioned about the outlet channel.

6. The interface device according to claim 1, further including a flange positioned about the first open end of the body.

7. The interface device according to claim 1, wherein the substantially cylindrical bore is a first substantially cylindrical bore and the body includes a plurality of substantially cylindrical bores including said first substantially cylindrical bore.

8. A method of infusing a catheter assembly, the method comprising the following steps:
i) providing the interface device as recited in claim 7 having a first fluid in the first reservoir;
ii) positioning a first syringe assembly into the first substantially cylindrical bore of the interface device, the syringe assembly defining a second fluid reservoir having a second fluid therein;
iii) securing the body of the interface device to a catheter assembly;
iv) advancing the syringe assembly within the first cylindrical bore to move the plunger from its retracted position to its advanced position to dispense the first fluid from the first reservoir into the catheter assembly;
vi) actuating the plunger assembly of the syringe assembly to dispense the second fluid from the second reservoir of the syringe assembly into the catheter assembly;
vi) positioning a second syringe assembly into a second of the substantially cylindrical bores, the second substantially cylindrical bore having a second plunger and defining a third reservoir having a third fluid therein and the second syringe assembly defining a fourth reservoir having a fourth fluid therein;
vii) advancing the second syringe assembly within the second substantially cylindrical bore to move the second plunger from its retracted position to its advanced position to dispense the third fluid from the third reservoir into the catheter assembly;
and viii) actuating a second plunger assembly of the second syringe assembly to dispense the fourth fluid from the fourth reservoir of the second syringe assembly into the catheter assembly.

9. The interface device according to claim 1, further including a first fluid located within the first reservoir.

10. The interface device according to claim 9, wherein the first fluid is saline.

11. A method of infusing a catheter assembly, the method comprising the following steps:
i) providing the interface device as recited in claim 1 having a first fluid in the first reservoir;
ii) positioning a first syringe assembly into the substantially cylindrical bore of the interface device the syringe assembly defining a second fluid reservoir having a second fluid therein;
iii) securing the body of the interface device to a catheter assembly;
iv) advancing the syringe assembly within the cylindrical bore to move the plunger from its retracted position to its advanced position to dispense the first fluid from the first reservoir into the catheter assembly; and
v) actuating the plunger assembly of the syringe assembly to dispense the second fluid from the second reservoir of the syringe assembly into the catheter assembly.

12. A method according to claim 11, wherein the first fluid is a flush solution and the second fluid is a lock solution.

13. A method according to claim 12, wherein the flush solution is saline and the lock solution is heparin.

* * * * *